United States Patent [19]

Saunders et al.

[11] 4,063,064

[45] Dec. 13, 1977

[54] APPARATUS FOR TRACKING MOVING WORKPIECE BY A LASER BEAM

[75] Inventors: Richard J. Saunders, San Jose; Wayne Sherman Mefferd, Los Altos Hills, both of Calif.

[73] Assignee: Coherent Radiation, Palo Alto, Calif.

[21] Appl. No.: 716,475

[22] Filed: Aug. 23, 1976

Related U.S. Application Data

[60] Division of Ser. No. 660,219, Feb. 23, 1976, which is a continuation of Ser. No. 524,585, Nov. 18, 1974, abandoned.

[51] Int. Cl.$^2$ .............................................. B23K 27/00
[52] U.S. Cl. ........................ 219/121 L; 219/121 LM; 424/15; 118/13; 118/15; 219/384; 219/158
[58] Field of Search ................. 219/121 Em, 121 EB, 219/121 LM, 121 L, 68, 159, 85 BA, 85 BM, 384; 118/13, 15, 18; 424/15, 19, 22; 423/659

[56] References Cited

U.S. PATENT DOCUMENTS

| | | | |
|---|---|---|---|
| 3,294,951 | 12/1966 | Olson | 219/85 BM X |
| 3,404,254 | 10/1968 | Jones | 219/121 EB |
| 3,562,377 | 2/1971 | Zetzsche | 264/155 |
| 3,808,394 | 4/1974 | Mominee | 219/121 LM X |
| 3,965,327 | 6/1976 | Ehlscheid | 219/121 LM X |
| 3,965,328 | 6/1976 | Locke | 219/121 LM X |

OTHER PUBLICATIONS

"The Tool and Manufacturing Engineer" – Precise Perforations 11/1969, H. Silvus, R. Bond, R. Swanson.

*Primary Examiner*—Bruce A. Reynolds
*Assistant Examiner*—Mark H. Paschall
*Attorney, Agent, or Firm*—Limbach, Limbach & Sutton

[57] ABSTRACT

Apparatus is disclosed in a system for drilling holes with a laser beam in a plurality of discrete moving workpieces carried by a support which moves each workpiece sequentially along a predetermined path at a predetermined velocity, the apparatus including means for sequentially tracking along a portion of such path each workpiece being drilled seriatim by the laser beam. This tracing apparatus includes means for directing the laser beam generally transversely of the direction of movement of the workpiece on the support and a mirror for folding the transversely directed laser beam toward the workpieces with means for oscillating the folding mirror synchronously with the movement of the workpiece to track the workpiece as it moves.

7 Claims, 10 Drawing Figures

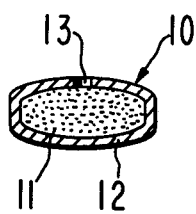
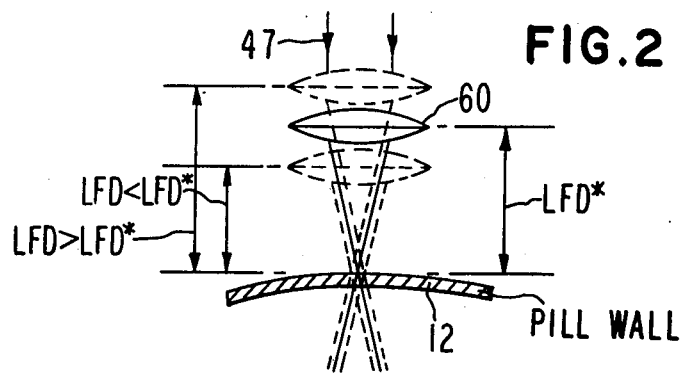
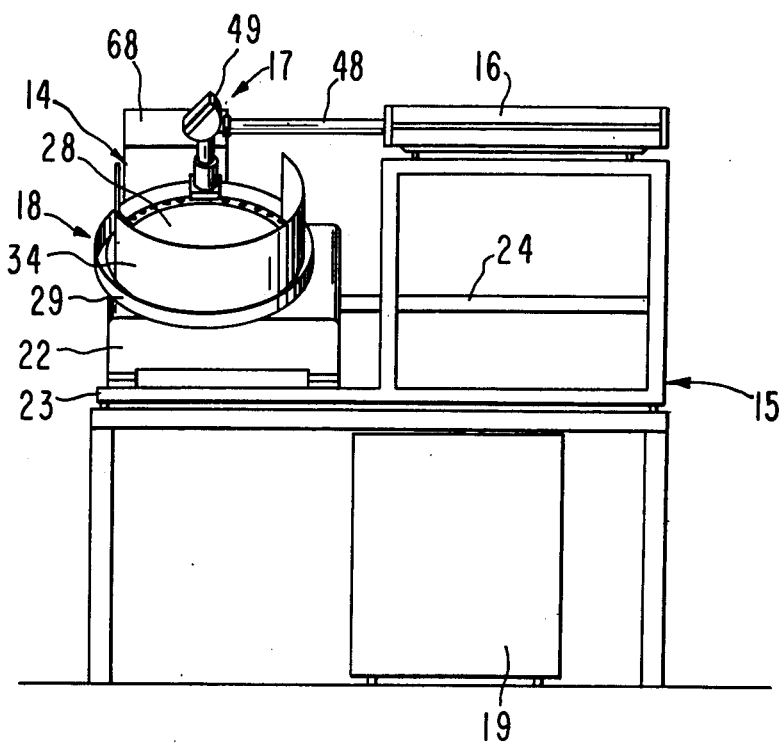
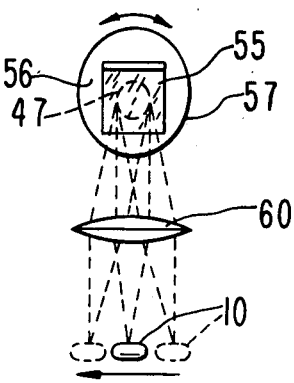

APPARATUS FOR TRACKING MOVING WORKPIECE BY A LASER BEAM

BACKGROUND OF THE INVENTION

Related Application

This application is a division of Patent Application Ser. No. 660,219, filed Feb. 23, 1976, which, in turn, is a continuation of Application Ser. No. 524,585 now abandoned, filed Nov. 18, 1974, in the name of Felix Theeuwes and Richard J. Saunders and Wayne Sherman Mefferd.

Field of the Invention

This invention relates to apparatus for causing a laser beam to track a moving object for a predetermined period of time. More specifically, it relates to laser tracking apparatus for use in forming holes in moving workpieces.

Description of the Prior Art

Lasers have been used to bore holes in watch jewels (U.S. Pat. No. 3,601,576), perforate thermoplastic sheets (U.S. Pat. No. 3,617,702), form holes in baby bottle nipples (U.S. Pat. No. 3,524,046) and perforate chemical-containing plastic packets ("Precise Perforations Every Time", Silvus et al, The Tool and Manufacturing Engineer, Nov. 1969, pp. 46–49). Defensive publication T903,014 discloses using a laser to print on pharmaceutical tablets.

SUMMARY OF THE INVENTION

The invention comprises apparatus for use with a laser beam for tracking moving workpieces such as pills thus to drill or form holes of an accurate predetermined size in the walls of the workpieces. The apparatus of this invention provides means for forming such holes accurately and rapidly in moving workpieces.

Briefly, the invention comprises apparatus for use in a system for drilling holes with a laser beam in a plurality of discrete moving workpieces carried by a support which moves each workpiece sequentially along a predetermined path at a predetermined velocity, the apparatus of the invention comprising structure for sequentially tracking along a portion of such path each workpiece being drilled seriatim by the laser beam and comprises means for directing said laser beam generally transversely of the direction of the movement of the workpiece on the support and a mirror for folding the transversely directed laser beam toward the workpiece on the support. Further included are means for oscillating the beam folding mirror synchronously with the movement of the workpiece, this mirror being oscillated between a first position directing the laser beam at a preselected point on the surface of the workpiece facing the folding mirror when the workpiece is at a location corresponding to the beginning of said path portion, and a second position directing the laser beam at the same said workpiece point when the workpiece is at a location corresponding to the termination of said path portion.

BRIEF DESCRIPTION OF THE DRAWINGS

In the drawings of this invention:
FIG. 1 illustrates the pills or workpieces drilled by the apparatus of this invention;
FIG. 2 is a schematic view illustrating the effect the position of the laser beam focusing lens through the pill wall has on the size and shape of the outlet passageways;
FIG. 3 is a partly schematic, front elevational view of the apparatus of this invention;
FIG. 4 is a schematic, diagrammatic view of the pill tracking apparatus used in the system of FIG. 3.

DETAILED DESCRIPTION OF THE INVENTION

Figure 5:
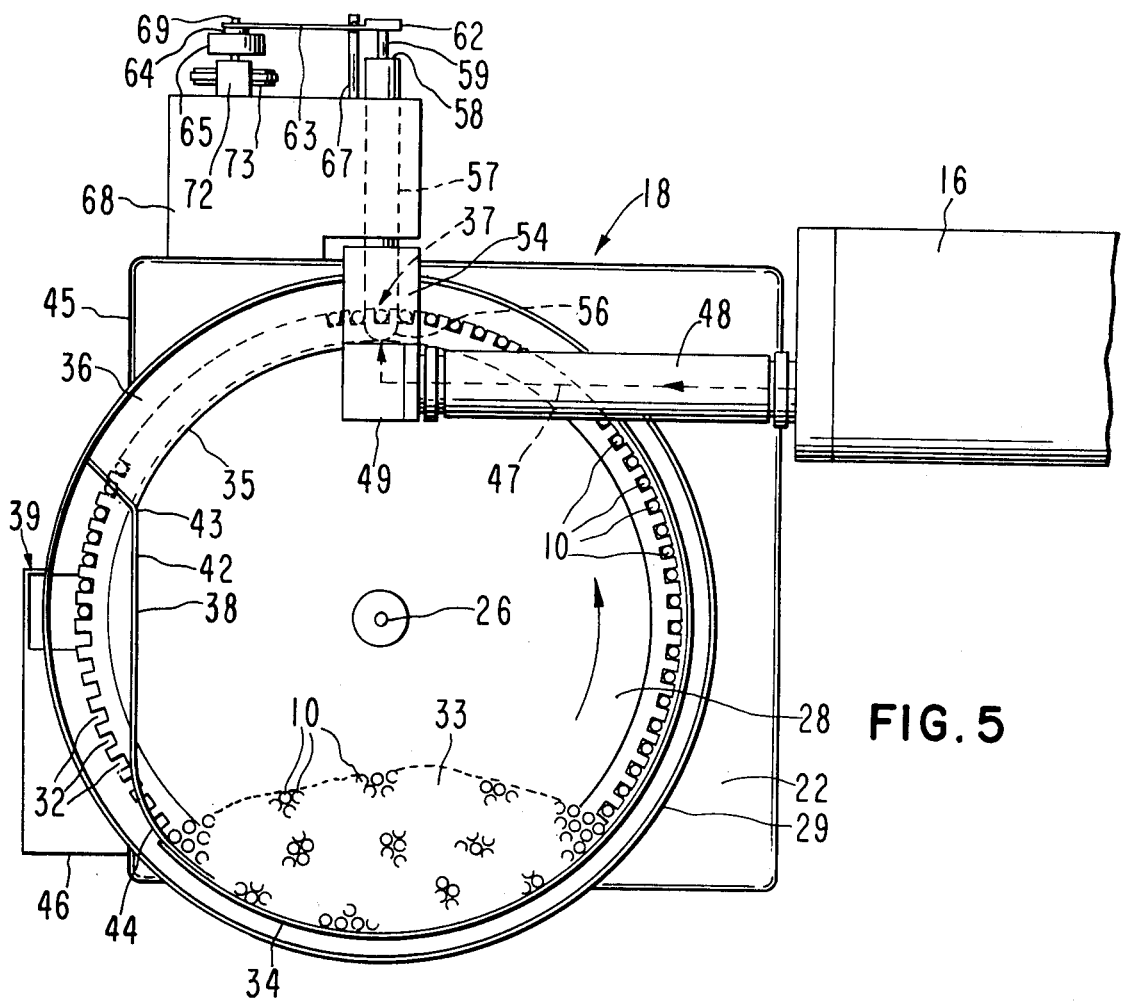
FIG. 5 is a top plan view of a portion of the system of FIG. 3.

FIG. 1 shows an embodiment, generally designated 10, of the pills to which the invention applies. Pill 10 comprises an inner core 11 surrounded by a wall 12 having an outlet passageway 13 (as formed per the invention process) in it. Core 11 must comprise a material which is an osmotically effective solute. In this respect it may comprise an active agent, such as a drug, which is itself an osmotic attractant or an active agent which itself is either an osmotically effective solute or not admixed with an inert osmotically effective solute additive such as an organic salt or a sugar. Wall 12 is formed at least in part of a semipermeable material, that is, it is permeable to the inward passage of water from the environment of use, e.g., gastrointestinal fluid, but substantially impermeable to the outward passage of the material(s) comprising core 11. Wall 12 will usually be between about 0.1 to 2000 microns thick. Since wall 12 functions as a pump housing it must maintain its integrity (not distend or disintegrate substantially) over the dispensing lifetime of pill 10. Materials from which osmosis and reverse osmosis membranes are made may be used to make wall 12. Examples of such materials are cellulose acetate, plasticized cellulose triacetate, agar acetate, amylose triacetate, -glucan acetate, acetaldehyde dimethyl acetate, cellulose acetate ethyl carbamate, cellulose acetate phthalate, cellulose acetate succinate, cellulose acetate dimethaminoacetate, cellulose acetate ethyl carbonate, cellulose acetate chloroacetate, cellulose acetate ethyl oxalate, cellulose acetate methyl sulfonate, cellulose ethers, poly(vinyl methyl) ether copolymers, cellulose acetate octoate, methyl cellulose, polyurethanes, hydrolyzed polyvinylacetate and hydroxylated ethylenevinylacetate copolymer.

Pill 10 dispenses its contents, i.e., core 11 as follows. Pill 10 is placed in an aqueous environment, such as a body cavity if core 11 contains a pharmaceutical. Core 11, being an osmotic attractant, causes water to permeate from the environment inwardly through wall 12. The water which has permeated through wall 12 dissolves a portion of the osmotically effective solute of core 11, forming a saturated solution. That solution exerts a hydrostatic pressure inside the device thereby dispensing the solution from the pill 10 out passageway 13.

As indicated above passageway 13 is critically sized to permit pill 10 to operate as an osmotic pump. In this regard passageway 13 must not be so large as to permit a significant amount of core 11 to diffuse outwardly through it relative to the amount of core 11 which is osmotically pumped out it (the ration of amounts should be less than about 0.1:1) and must not be so small as to cause pressure to accumulate within pill 10 in excess of that which would burst wall 12 open. It has been found that passageways in the range of about 4 microns to about 2000 microns in diameter will usually meet the above described functional criteria. Preferably the passageway diameter will be in the range of about 75 microns to about 350 microns.

FIG. 3 depicts apparatus, generally designated 14, for forming passageway 13. Apparatus 14 includes a support frame, generally designated 15, a laser 16, an optical pill tracking mechanism, generally designated 17, a rotary pill indexer, generally designated 18, and an electrical power supply/control 19 which supplies and controls the power for laser 16, tracking mechanism 17 and indexer 18.

Indexer 18 is the portion of apparatus 14 which moves pills 10 in succession along a predetermined path at a predetermined velocity. It is substantially identical in structure and operation to the pill indexer units used in the pharmaceutical industry to print trademarks, designs or other designations on pills. Indexer 18 includes a housing 22 which is bolted to frame members 23, 24 (FIG. 3). Because the vertical position of frame member 23 is lower than the vertical position of frame member 24, indexer 18 is inclined rearwardly. As discussed hereinafter this inclination facilitates charging the pills to indexer 18. An electrical motor 25 (FIG. 6) is contained within housing 22 and is connected (not shown) to power supply 19. Motor 25 has a driving shaft 26 which extends upwardly through an aperture (not shown) in the top 27 of housing 22. An indexing wheel 28 is fixedly mounted on the end of driving shaft 26. Wheel 28 sits freely within a drum 29 attached to top 27 of housing 22 and has a plurality of slots 32 spaced equidistantly around its periphery. Slots 32 are adapted in size and shape to receive pills 10 (FIG. 5). As seen in FIG. 5 a hopper at 33 for pills 10 is defined by the upper surface of wheel 28 and by a fixed arcuate wall 34 which extends upwardly from the bottom of drum 29 and around and closely adjacent to about half the periphery of wheel 28. Pills 10 fall by gravity from the hopper at 33 into slots 32 with their bottoms engaging the surface of the bottom of drum 29. A cover 35 comprising a generally horizontal wall 36 and an integral generally vertical wall (not shown) encloses a section of the edge of wheel 28 immediately downstream from a passageway forming station (indicated generally at 37). Cover 35 prevents pills 10 in which a passageway 13 has been formed from returning to the hopper 33. A generally vertical wall 38 joins cover 35 and wall 34 and prevents pills 10 in hopper 33 from being discharged from indexer 18 at the pill discharge station thereof, indicated at 39. Wall 38 is comprised of a chordal portion 42 having an end 43 joined to cover 35 and an integral arcuate portion 44 which extends into overlapping adjoinment with the inner surface of wall 34. The lower edge of wall 38 is spaced just above the surface of wheel 28.

Figure 6:
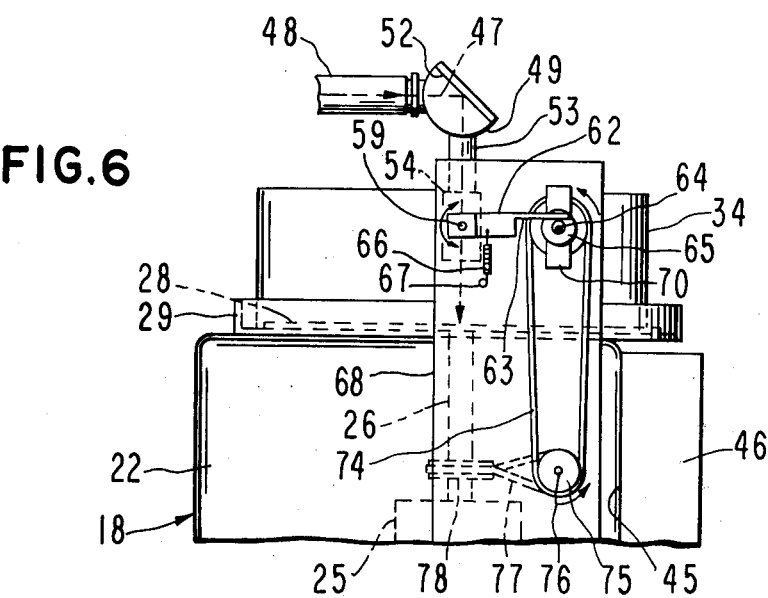
FIG. 6 is a rear elevational view of a portion of the system of FIG. 3 illustrating the drive mechanism which synchronizes the pill or workpiece movement with a laser tracking and firing.

As seen in FIG. 6 portions of wheel 28 and drum 29 overhang the side 45 of housing 22. Drum 29 has a hole (not shown) in the bottom of its overhanging portion through which pills 10 in which a passageway 13 has been formed may drop. A collecting bin 46 is positioned below that hole to catch the pills 10 dropping therethrough.

Optical tracking mechanism 17 is the portion of apparatus 14 which receives a beam (indicated by a dashed line 47 in FIGS. 2 and 6) from laser 16 and tracks the pills 10 being carried in the slots 32 of wheel 28 seriatim with the beam. Beam 47 is generated within laser 16 which is mounted horizontally on the top of support frame 15. The wavelength of the laser beam should be readily absorbable by the material of wall 12 of pill 10. Most of the wall 12 materials described hereinbefore efficiently absorb energy in the range of 9–12 microns wavelength. Conventional $CO_2$ lasers produce a beam of approximately 10.6 microns wavelength and accordingly may be used with most wall materials. Lasers having higher or lower wavelengths than a $CO_2$ laser may be used, but the absorbtion of their energy output by the pill wall will be less efficient. The use of such lasers will require greater power and/or firing duration to form passageways 13. For use in the invention process laser 16 must be adapted to operate in a pulsed mode, desirably at an average power in the range of 1 to 100 watts and preferably in the range of 15 to 30 watts in the case of a $CO_2$ laser.

Beam 47 exits from laser 16 and travels horizontally through a tubular shield 48, an end of which is coupled to the exit port of laser 16 and the other end of which is coupled to one end of a hollow elbow 49 (FIG. 5). A 45° angle mirror 52 housed within elbow 49 reflects beam 47 90° downwardly (FIG. 6) into tubular member 53 which is coupled to the other end of elbow 49.

The lower end of tube 53 is coupled to a hollow housing 54 (FIG. 6). A second 45° angle mirror (not shown) having a rearward decline is mounted within housing 54 in the path of beam 47. As shown diagrammatically in FIG. 5 beam 47 is reflected by said second 45° angle mirror 90° rearwardly onto a tracking mirror 55 (FIG. 4) affixed to front end 56 of cylindrical tracking mirror mount 57. End 56 is elliptical in shape and declines rearwardly at a 45° angle (i.e. it defines a cylindrical section at 45° to the axis) and thus tracking mirror 55 also declines rearwardly at a 45° angle. Tracking mirror 55 reflects beam 47 90° in a generally downward path in the plane of the major axis of end 56 through a focusing lens 60 (FIG. 4) mounted in housing 54. Mount 57 extends generally horizontally through the rear wall of housing 54 to a position such that tracking mirror 55 is aligned directly above the slotted edge of wheel 28 at tracking station 37. Mount 57 is journalled and received within housing 54 such that it is free to oscillate rotationally (illustrated by solid double arrowheaded lines in FIGS. 4 and 6).

FIGS. 5 and 6 illustrate the mechanism which drives tracking mechanism 17, that is oscillates mount 57, in time with the rotation of wheel 28. Rear end 58 of mount 57 has an axial shaft 59 extending from it. One end of a cam follower 62 is fixedly attached to the end of shaft 59. The other end of follower 62 forms a lever arm 63 which rides on an eccentric pin 64 of a cam wheel 65. The engagement between arm 63 and pin 64 is maintained by a spring 66 attached between follower 62 and a horizontal rod 67 which extends rearwardly from the back of extension 68 of housing 22. Cam wheel 65 is attached to an end of a shaft 69 which is journalled in a C-shaped saddle 72 and within extension 68. Shaft 69 has a driven timing sheave 73 positioned inwardly of cam wheel 65. A timing belt 74 connects sheave 73 with a pulley 75 mounted on a shaft 76 journalled within extension 68. Shaft 76 also carries another pulley (not shown) inwardly of pulley 75 which is connected by a belt 77 to a pulley 78 mounted on shaft 26 of motor 25.

The above described passageway forming apparatus 14 operates as follows. Pills 10 in which passageways 13 are to be formed are charged into hopper 33 and drop by gravity from hopper 33 into slots 32 of rotating feed wheel 28 (FIG. 5). Wheel 8 carries the pills in a circular path at a velocity determined by the speed of motor 25 to passageway forming station 37. At station 37 each pill is tracked by optical tracking mechanism 17 which sweeps repeatedly approximately 1° of the arc of the circular path along which the pill 10 is being carried by wheel 28. As shown in FIG. 4 the tracking is accomplished by the rotational oscillation of mount 57 and tracking mirror 55. The tracking velocity is synchronized with the velocity at which pill 10 is moving because tracking mechanism 17 and wheel 28 are both driven by motor 25. During the tracking laser 16 is fired and emits beam 47. The firing is triggered by a magnetic sensor (not shown) located at a fixed position relative to cam wheel 65 which responds to a magnetic button (not shown) imbedded in the surface of cam wheel 65. As cam wheel 65 rotates, each pass of the magnetic button past the sensor triggers the laser. As mentioned above laser 16 is adapted to pulse mode operation and the duration for which beam 47 is emitted will depend on the pulse setting of laser 16. The duration must, of course, be correlated with the other process variables described herein. Durations in the range of about 0.1 to about 10 milliseconds will usually be employed. Beam 47 is transmitted by optical tracking mechanism 17 onto the surface of the moving pill 10 and moves with the moving pill (FIG. 4) as mirror 55 oscillates clockwise. The energy of beam 47 is absorbed by the material of wall 12 of pill 10, causing the material to heat and ultimately be pierced by the beam, thus forming passageway 13.

At the completion of the tracking mirror 55 oscillates counterclockwise back to its starting position to track the next succeeding pill.

Hole forming station 37 may optionally be equipped with means for maintaining the focusing lens-to-pill wall distance constant despite variations in the overall pill thickness. This means (not shown in the drawings) may comprise a vertically adjustable reference shoe which surrounds but does not interrupt the optical path of the laser beam and is affixed to the lens housing and extends downwardly therefrom such that the distance from the lens to the bottom edge of the shoe is equal to the desired lends to pill wall distance. Combined with the reference shoe is means, such as a spring or air jet, underlying station 37 which engages the pill and urges it upwardly against the bottom edge of the reference shoe while the pill is at station 37.

After a pill 10 clears hole forming station 37 it continues to be carried in a circular path by wheel 28. Cover 35 and wall 38 prevent any pill in which a passageway has been formed and which is prematurely ejected from the slot 32 in which it is riding from returning to hopper 33. When the laser drilled pills 10 reach discharge station 39 they drop through the hole in the bottom of the overhanging portion of drum 29 into bin 46.

Assuming efficient absorbtion of the laser beam 47 by the material of wall 12, the size of passageway 13 will depend upon the laser power, firing duration (pulse time), thickness of wall 12 and the dimensions of beam 47 at the wall 12. As illustrated in FIG. 2 the dimensions of beam 47 at wall 12 also affect the shape of passageway 13 and are a function of the distance between focusing lens 60 and wall 12. In FIG. 2 the distance between the lens and the wall 12 is generally designated LFD (lens focusing distance), with LFD* designating the LFD which is equal to the focal length of the lens. When LFD is less than LFD* wall 12 is struck with a convergent beam causing passageway 13 to be frustoconical in shape rather than cylindrical. When LFD is equal to or greater than LFD* wall 12 is confronted by a divergent beam which, it has been found, forms a generally cylindrical hole. For this reason it is desirable that LFD's equal to or greater than LFD* be employed.

Figure 7:
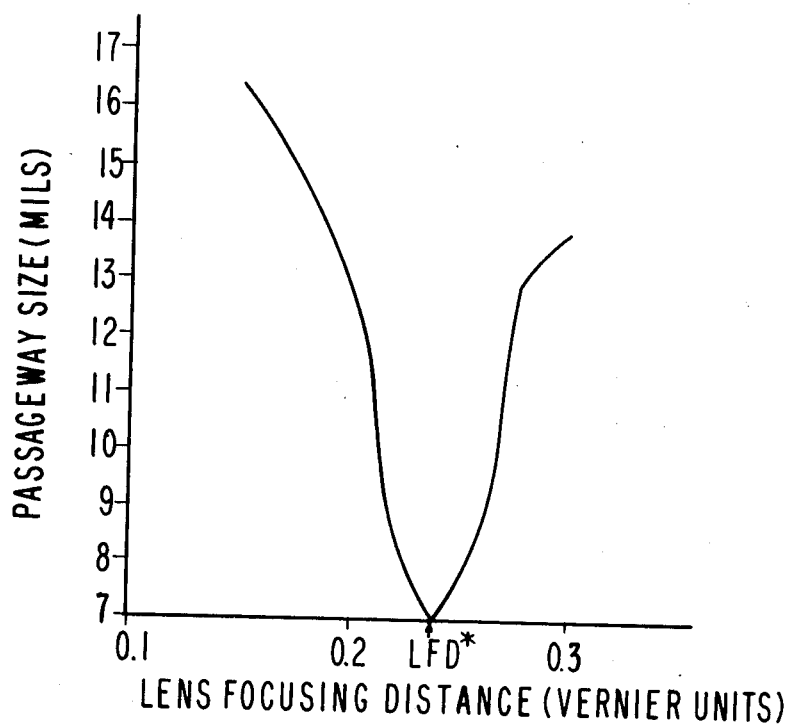
FIG. 7 is a graph showing the relationship between the passageway size and the distance of the lens from the pill wall at a fixed wall thickness, laser power and firing duration.

It was also found that when the aforementioned variables are held constant, that the smallest passageway is formd when LFD = LFD*. This is graphically shown in FIG. 7. The plot of FIG. 7 was developed with a $CO_2$ laser (Coherent Radiation Model 42) set at 50 watts power and 0.6 millisecond firing duration. The wall was 65 microns thick cellulose acetate. Passageways were formed at various LFD's (reported as the vernier reading on the lens vertical adjuster) and measured with an optical comparator. It should be noted that the vernier LFD readings are inversely related to the actual LFD, that is, lesser vernier LFD readings denote greater actual LFD's and vice versa.

Figure 8:
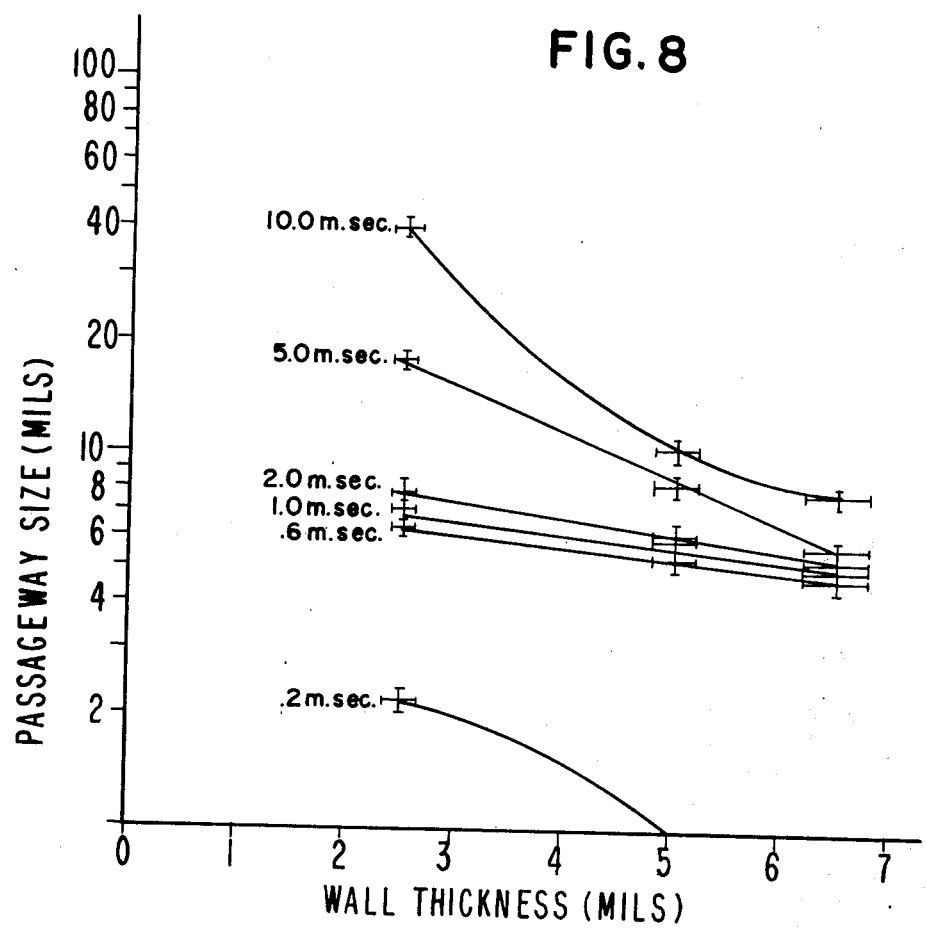
FIGS. 8, 9 and 10 are graphs illustrating the relationship between the passageway size, wall thickness and firing duration at a fixed laser power at three different pill wall to lens distances.

FIG. 8 shows graphically passageway size as a function of wall thickness at various firing durations. The plots of FIG. 8 were developed with the $CO_2$ laser described above set at 50 watts power. The LFD was LFD*. Passageways were formed in cellulose acetate walls 65, 130 and 165 microns thick at the indicated firing durations and were measured with an optical comparator.

Figure 9:
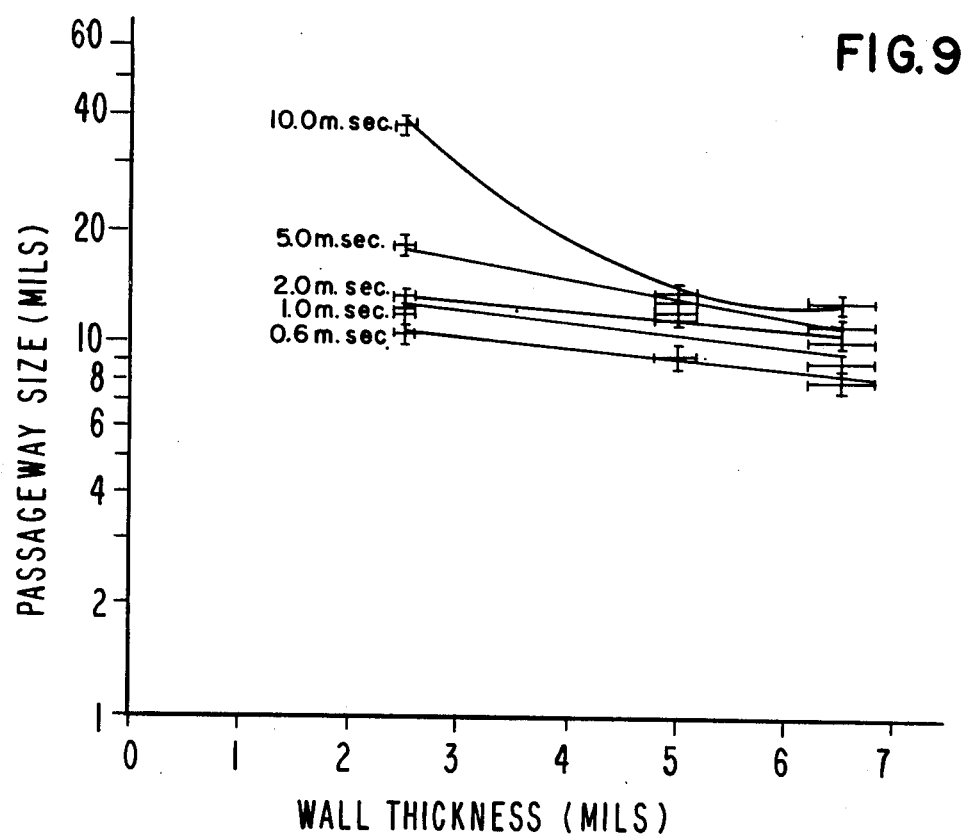
Figure 10:
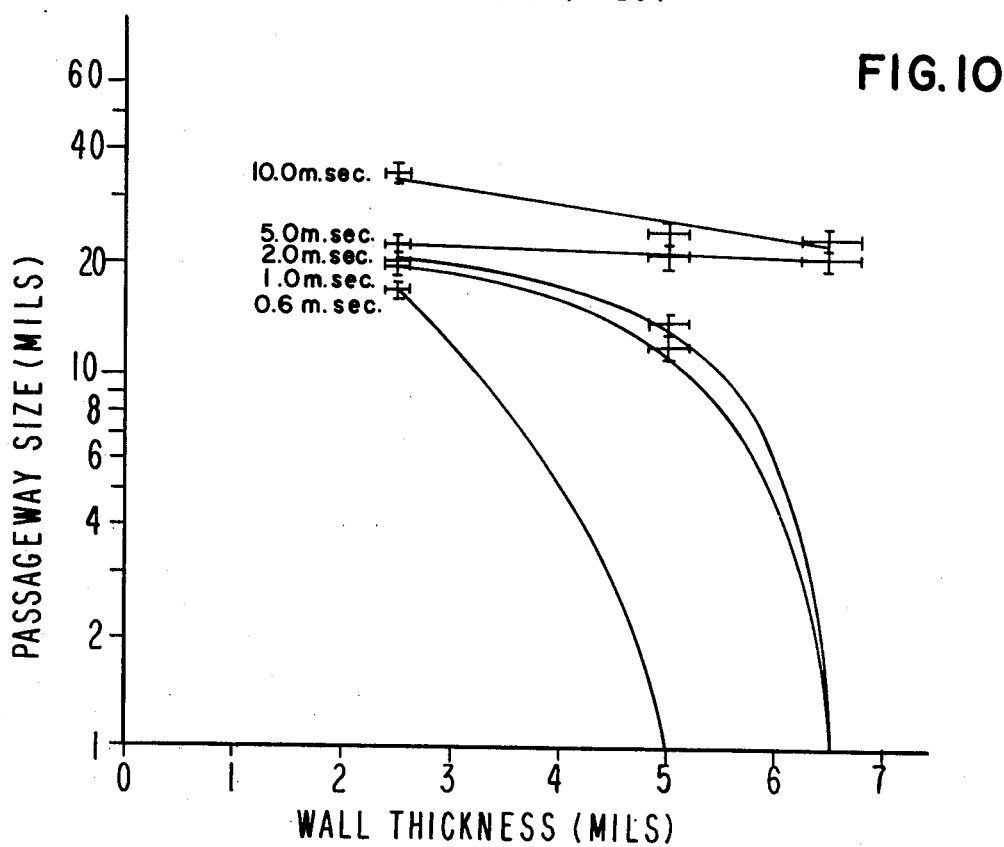

The graphs of FIGS. 9 and 20 were made in the same manner LFD vernier readings of 0.15 and 0.20, respectively (see FIG. 7) were used.

The graphs of FIGS. 7-10 illustrate the relationship between the above mentioned process variables except laser power. Passageway size will increase with increasing laser power, all other variables being held constant.

Modifications of the above described apparatus which are obvious to those of skill in the mechanical, laser and/or pill handling arts are intended to be within the scope of the following claims.

What is claimed is:

1. A system for drilling holes with a laser beam in a plurality of discrete moving workpieces comprising
    a support which moves said plurality of discrete workpieces sequentially along a predetermined path at a predetermined velocity, and
    apparatus for sequentially tracking along a portion of such path each said workpiece being drilled seriatum by said laser beam, said tracking apparatus comprising
    means for directing said laser beam generally transversely of the direction of movement of said workpiece on said support;
    a mirror for folding said transversely directed laser beam toward said workpiece on said support; and
    means for oscillating said beam folding mirror synchronously with the movement of said workpiece, said mirror being oscillated between a first position directing said laser beam at a preselected point on the surface of said workpiece facing said folding mirror when said workpiece is at a location corresponding to the beginning of said path portion, and a second position directing said laser beam at the same said workpiece point when said workpiece is at a location corresponding to the termination of said path portion, whereby, during the portion of the mirror oscillation from the first position to the second position the laser beam is caused to track the preselected point on each workpiece; and a focusing lens positioned between said oscillating beam folding mirror and said workpiece for focusing said laser beam upon said workpiece surface and maintaining that focus throughout the tracking of said workpiece by said laser beam.

2. A system according to claim 1 further comprising means for discontinuing the laser beam during the portion of said mirror oscillation from said second position to said first position.

3. A system according to claim 1 wherein said moving support comprises a rotary transport wheel rotating about its center with said workpieces positioned adjacent the periphery of said indexing wheel.

4. A system according to claim 1 wherein said oscillating means comprises a cam drivingly connected to said moving support for synchronization with the movement of said support and said workpieces thereupon, and a cam follower connected to an axially rotatable shaft to which is affixed said beam folding mirror, whereby rotation of the cam synchronously with the moving support and object provides synchronous actuation of the cam follower and thus synchronous oscillation of the beam folding mirror for tracking of the workpieces by the laser beam.

5. A system according to claim 1 wherein said focusing lens is maintained stationary and at a fixed distance from said support while said beam folding mirror is oscillated, whereby oscillation of the beam folding mirror serves to sweep the laser beam across the lens while maintaining the focus of the beam relative to the moving support.

6. A system according to claim 6 further comprising means for maintaining a constant preselected distance between said focusing lens and the point on said workpiece upon which said laser beam is directed irrespective of differences in workpiece thickness, said distance maintaining means comprising a member positioned between said focusing lens and said workpiece having an aperture for passage of said laser beam therethrough and having a reference surface adjustably positionable longitudinally of said laser beam between said focusing lens and said object, and means urging said workpiece against said reference surface, whereby the surface of each workpiece is brought into the proper relationship with the focal point of the laser beam for drilling each such workpiece.

7. A system according to claim 6 wherein said workpiece urging means comprises a resilient spring.

* * * * *